US006350433B1

(12) United States Patent
Ashton et al.

(10) Patent No.: US 6,350,433 B1
(45) Date of Patent: *Feb. 26, 2002

(54) AUTOPHOBIC HAIR SPRAY COMPOSITION COMPRISING FILM FORMING RESIN, PROPELLANT, AND AUTOPHOBIC HAIR SPRAY ADDITIVE

(75) Inventors: Melanie Ruth Ashton, Wirral (GB); Llyr Glyndwr Griffiths, Le Meux (FR); Anthony Moretta, Wirral (GB)

(73) Assignee: Unilever Home & Personal Care USA, Division of Conopco, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/275,151

(22) Filed: Mar. 24, 1999

(30) Foreign Application Priority Data

Mar. 24, 1998 (GB) ............................................. 9806295

(51) Int. Cl.⁷ .................................................. A61K 7/11
(52) U.S. Cl. ..................... 424/45; 424/47; 424/DIG. 1; 424/DIG. 2; 424/70.11; 514/63
(58) Field of Search ....................... 424/45, 47, DIG. 1, 424/DIG. 2, 70.11; 514/63

(56) References Cited

U.S. PATENT DOCUMENTS

| 3,822,238 A | 7/1974 | Blair et al. |
| 4,156,066 A | 5/1979 | Gould |
| 4,156,067 A | 5/1979 | Gould |
| 4,255,550 A | 3/1981 | Gould |
| 4,743,673 A | 5/1988 | Johnston et al. |
| 4,859,455 A | 8/1989 | Nowak, Jr. et al. |
| 4,871,529 A | 10/1989 | Sramek |
| 5,000,955 A | 3/1991 | Gould et al. |
| 5,021,238 A | 6/1991 | Martino et al. |
| 5,176,898 A | 1/1993 | Goldberg et al. |
| 5,435,993 A | 7/1995 | Hamilton et al. |
| 6,056,946 A | * 5/2000 | Crudele et al. |
| 6,106,808 A | * 8/2000 | Bhatt et al. |
| 6,106,809 A | * 8/2000 | Bhatt et al. |
| 6,113,881 A | * 9/2000 | Bhatt et al. |
| 6,132,704 A | * 10/2000 | Bhatt et al. |
| 6,274,129 B1 | * 8/2001 | Bhatt et al. |
| 6,284,225 B1 | * 9/2001 | Bhatt et al. |

FOREIGN PATENT DOCUMENTS

| DE | 4421562 | 12/1995 |
| EP | 0590604 | 4/1994 |
| EP | 0619111 | 12/1996 |
| EP | 0796611 | 9/1997 |
| WO | 93/03704 | 3/1993 |
| WO | 97/46213 | 12/1997 |
| WO | 99/17711 | 4/1999 |

* cited by examiner

*Primary Examiner*—Raj Bawa
(74) *Attorney, Agent, or Firm*—Matthew Boxer

(57) ABSTRACT

A single-phase autophobic hairspray composition containing 0.5% to 10% by weight of a film-forming hairspray resin; 10% to 60% by weight of a binary mixed propellant system; 0.01% to 1.0% by weight of an autophobic silicone hairspray additive; and 10% to 25% by weight water, is described.

7 Claims, No Drawings

AUTOPHOBIC HAIR SPRAY COMPOSITION COMPRISING FILM FORMING RESIN, PROPELLANT, AND AUTOPHOBIC HAIR SPRAY ADDITIVE

FIELD OF THE INVENTION

The invention relates to an aerosol hairspray composition to achieve styling with improved sensory attributes at high water levels.

BACKGROUND AND PRIOR ART

Hairspray compositions must meet a number of functional requirements. These include good holding ability and curl retention without giving a harsh, brittle feeling to the hair.

Conventional hairspray formulations are ethanol based and therefore form highly wetting systems for hair. Coalescence of the aerosol droplets on the hair fibre and subsequent ethanol evaporation to leave solid polymer residue leads to a network of fibre-fibre bonds.

There are, however, undesirable consequences in coating hair with polymer, manifesting in perceptions of sensory negatives such as stiffness, rigid feel, stickiness or unnatural feel.

U.S. Pat. No. 4,871,529 describes ethanol solvent-based hairspray compositions which employ a specific type of silicone copolyol which causes the hairspray composition to contract upon drying. This is described as an "autophobic effect" which causes large droplets of the composition to form, and produce larger juncture points between fibres. Localisation of deposits in this way is advantageous since it offers stronger bonds and more durable hold, yet reduced sensory negatives such as stiffness and unnatural feel.

U.S. Pat. No. 4,871,529 advises the minimum amount of water in its autophobic systems, if water is present at all. Increasingly, however, with the advent of legislation concerning the volatile organic content of hairsprays, it is desirable to formulate systems with relatively high water content.

U.S. Pat. No. 5,021,238 (Martino et al.) reports the advance of using dimethyl ether (DME) as a hairspray propellant. DME allows use of water as the only solvent thereby significantly reducing the volatiles problem.

However, with this type of propellant it has proved impossible to achieve an autophobic effect at high water levels.

Alternatively, replacement of chlorofluorocarbons with hydrocarbon propellants has been discussed in U.S. Pat. No. 4,859,455 (Nowak, Jr. et al).

However, a problem with hydrocarbon propellants is that it becomes impossible to achieve a single phase system at high water levels. For example, in a water-hydrocarbon system containing more than 15% hydrocarbon, the composition separates into two phases—an aqueous phase and a hydrocarbon phase.

We have now found that achievement of both an autophobic effect and a single phase system is possible through use of a specific mixture of propellants in combination with a film-forming hairspray resin and an autophobic hairspray additive. Moreover the autophobic effect thus achieved is tolerant to high water levels.

SUMMARY OF THE INVENTION

The invention provides a single phase autophobic hairspray composition comprising:

a) from 0.5% to 10% by weight of a film-forming hairspray resin;
b) from 10 to 60% by weight of a propellant including a mixture of at least one hydrocarbon and a di($C_1$–$C_4$ alkyl) ether in a weight ratio from 5:1 to 1:10;
c) from 0.01% to 1.0% by weight of an autophobic hairspray additive, being a surfactant or polymer which imparts autophobic behaviour to the hairspray composition, and
d) water.

DETAILED DESCRIPTION OF THE INVENTION

Film-Forming Hairspray Resin

The hairspray resins employed in compositions of the present invention should be capable of forming a film and holding the hair of the user in place after evaporation of the volatile components of the hairspray composition.

Hairspray resins are well known articles of commerce and many such resinous polymers are available commercially which contain moieties which render the polymers cationic, anionic, amphoteric or nonionic in nature. To provide optimum sprayability, the polymers employed in hairspray compositions typically range in number average molecular weight of from 5,000 to 100,000 with 10,000 to 50,000 being more preferred.

The amount of the resin may range from 0.5 to 10%, preferably 0.75 to 6% by weight of the total composition.

Examples of anionic hairspray resins are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers, terpolymers, etc., containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate, acrylamide; alkyl acrylamides and methacrylamides having 1 to 8 carbon atoms in the alkyl group (such as methacrylamide, t-butyl acrylamide and n-octyl acrylamide), and other compatible unsaturated monomers. The polymer may also contain grafted silicone, such as polydimethylsiloxane.

One specific example of a suitable anionic hairspray resin is the emulsion polymerised terpolymer of methacrylic acid, n-butyl acrylate and ethyl acrylate (e.g. in a weight percent ratio of 31:42:27, respectively). Another specific example is Ultrahold® 8 (CTFA-Cosmetic, Toiletries and Fragrance Association designation of Acrylate/Acrylamide Copolymer).

Other suitable anionic hairspray resins include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP 0 619 111 A1 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hairspray resin is Amphomer® (octylacrylamide/acrylates/butylaminoethyl methacrylate copolymer) sold by the National Starch and Chemical Corporation.

Examples of nonionic hairspray resins are homopolymers of N-vinylpyrrolidone and copolymers of N-vinylpyrrolidone with compatible nonionic monomers such as vinyl acetate and terpolymers of ethyl acrylate, butyl methacrylate and methyl methacrylate. Nonionic polymers containing N-vinylpyrrolidone in various weight average molecular weights are available commercially from ISP Corporation such as homopolymers of N-vinylpyrrolidone having an average molecular weight of about 630,000 sold by ISP (formerly GAF Corporation) under the tradename PVP K-90 and those having an average molecular weight of about 1,000,000 sold under the trademark of PVP K-120.

Examples of cationic hairspray resins are copolymers of amino-functional acrylate monomers such as lower alkyl aminoalkyl acrylate or methacrylate monomers such as dimethylaminoethyl methacrylate with compatible monomers such as N-vinylpyrrolidone, vinyl caprolactam, or alkyl methacrylates such as methyl methacrylate and ethyl methacrylate and alkyl acrylates such as ethyl acrylate and n-butyl acrylate.

Cationic resins containing N-vinylpyrrolidone are commercially available from ISP Corporation such as those sold under the trademarks of Copolymer 845 and Copolymer 937 (copolymers of N-vinylpyrrolidone and t-butylaminoethyl methacrylate of average molecular weight about 1,000,000) and Gafquat® 755 and 755N (quaternary ammonium polymers formed by the reaction of dimethyl sulfate and a copolymer of N-vinylpyrrolidone and dimethylaminoethyl methacrylate of average molecular weight about 1,000,000).

With certain of the resins it may be necessary to neutralise some acidic groups to promote solubility/dispersibility.

Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as lauramidopropyl dimethylamine may be employed, as is described in U.S. Pat. No. 4,874,604. Mixtures of any of the above neutralising agents may be used. Amounts of the neutralising agents will range from about 0.001 to about 10% by weight of the total composition.

Propellant

Essential to the present invention is a mixed propellant system of hydrocarbon and dialkyl ether. The dialkyl ether is a di($C_1$–$C_4$ alkyl) ether, most preferably dimethyl ether. The hydrocarbon component of the propellant system will be a $C_3$–$C_5$ alkane, especially one selected from propane, isobutane, n-butane and mixtures thereof. An example is a combination of propane and isobutane, such as A50 propellant commercially available from the Aeropress Corporation.

Total amount of propellant will range from 3 to 50%, preferably from 5 to 45%, optimally from 25 to 45% by weight of the total composition.

Weight ratios of total hydrocarbon to dialkyl ether will range from 5:1 to 1:10, preferably from 2:1 to 1:5, more preferably from 1:1 to 1:4, optimally about 1:2 by weight.

Autophobic Hairspray Additive

Also essential to the present invention is an autophobic hairspray additive, being a surfactant or polymer which imparts autophobic behaviour to the hairspray composition.

Autophobic behaviour of the hairspray composition can conveniently be evaluated as follows:

Conventional systems display high wetting of hair fibres. In these systems, solid (including hairspray resin) deposited in fibre-fibre junctions is significantly spread along the fibres from the centre of the junction along the length of the fibres. In contrast, autophobic systems appear to localise deposition at fibre-fibre junctions, with a reduced coating of those fibre regions external to the junctions. This is consistent with the deposit being formed from a poorly wetting system, that is, the liquid makes a high contact angle with the fibre. The high contact angle droplet morphology of the dried autophobic system on crossed hair fibres can be viewed by magnifying lens.

Suitable autophobic hairspray additives may be selected from the group consisting of:

(i) alkyl-pendant silicone copolyols of formula (I):

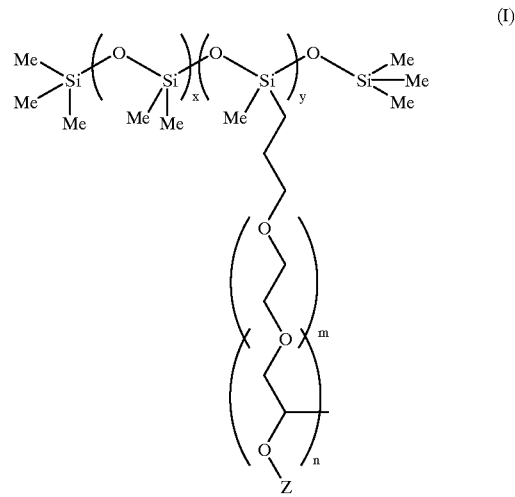

where m and n are integers of from 0 to 50, and x and y are integers chosen to give the copolyol a molecular weight of at least 600. Z is hydrogen or a C1-4 alkyl radical;

(ii) dimethicone copolyols of formula (II):

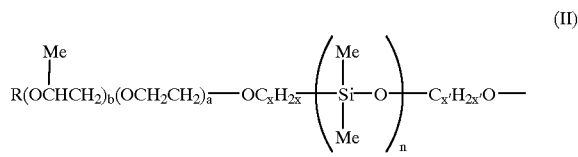

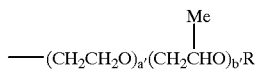

where n is an integer chosen to give the copolyol a molecular weight of at least 600;

x and x' are integers of from 1 to 12;

a, a',b, b' are integers of from 0 to 50, and R is hydrogen or a C1-4 alkyl radical;

(iii) polydimethicone copolyols of formula (III):

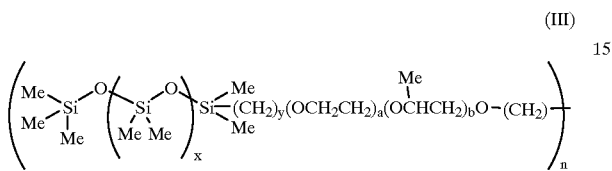

where x and n are integers chosen to give the copolyol a molecular weight of at least 500;
y is an integer of from 1 to 12, and
a and b are integers of from 0 to 50;

(iv) alkyl ethoxylates; and (v) fluorosurfactants.

Illustrative alkyl-pendant silicone copolyols of formula (I) as referred to above are described in U.S. Pat. No. 4,871,529. A preferred example is the ethoxylated dimethicone copolyol SILWET® L-7602, ex OSi Specialities.

Dimethicone copolyols of formula (II) referred to above are sometimes designated as "ABA" type copolymers, due to the presence of alternating polyalkylene oxide and silicone blocks.

Polydimethicone copolyols of formula (III) referred to above are sometimes designated as (AB)n type copolymers.

The molecular weight of the copolyols of formulae (II) and (III) suitably ranges from 500 to 50,000.

Suitable dimethicone copolyols of formula (II) are SIL-SOFT® 900, sold by OSi Specialties, having a molecular weight of about 2000, with R being hydrogen and a being 0, and the materials sold by Goldschmidt as TEGOPRENO® 3012 and 5830 respectively.

Suitable polydimethicone copolyols of formula (III) are those described in U.S. Pat. No. 4,242,466. Illustrative is the material sold by OSi Specialties as SILSOFT® 487, having a molecular weight of about 150,000, with a and b both greater than 0.

Examples of suitable alkyl ethoxylates are those of general formula (IV):

$C_nH_{2n+2}(OCH_2CH_2)xOR$ (IV)

where n is an integer of from 5 to 20, preferably from 8 to 18, most preferably 12 to 14;

x is an integer of from 3 to 50, preferably from 3 to 30; and

R is hydrogen or a $C_{1-4}$ alkyl group, e.g. methyl. Preferably R is hydrogen.

Illustrative are GENAPOL® C-250, (ex Hoechst Celanese), 1which is coconut fatty alcohol (C8–C18, mainly C12–C14) ethoxylated with 25 moles of ethylene oxide, and DOBANOL® 91-5 (ex Shell), which is C9–C11 alcohol ethoxylated with 5 moles of ethylene oxide.

Fluorosurfactants are surfactants in which the hydrophobic segment of the molecule contains fluorine. At least one hydrogen atom in the hydrophobic segment contains fluorine. The hydrophobe can be fully fluorinated (perfluorinated) or partially fluorinated. As with conventional surfactants, fluorosurfactants can be classified into four types: anionic, cationic, amphoteric and nonionic. Their structural features are described in the book "Fluorinated Surfactants —Surfactant Science Series Vol. 50" by Eric Kissa, Marcel Dekker Inc., 1994, Chapter 1.

An example of a suitable fluorosurfactant is the material sold by Dow/3M as L13564, of formula (V):

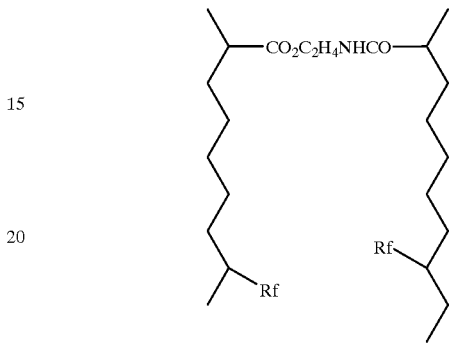

where $R_f$ is a fluorine containing hydrophobe.

Mixtures of any of the above autophobic hairspray additives may also be used.

Water

Compositions of the present invention include water.

Typical water levels for an ethanol-based aerosol fixing spray are from 2 to 10%, usually about 2 to 6% by weight.

However, with the advent of legislation concerning the flammability and volatile organic content of hairsprays, it is increasingly desirable to formulate systems with relatively high water content. A particular advantage associated with hairsprays according to the present invention is that they can be formulated with high water content, without prejudice to the autophobic effect.

Hairsprays of the present invention can be formulated with a water content of up to 30%, even 45 to 55%, by weight of the total composition. The upper water content limit is not critical to the present invention, but in general is governed by the tendency of the hairspray formulation to impart a sticky feel to the hair if the level of water is too high.

An optimum water level for hairsprays of the present invention is generally from 10 to 25%, e.g. around 15 to 20% by weight of the total composition.

Optional Components

A preferred optional component in hairsprays of the invention is a conditioning agent selected from volatile and non-volatile silicone fluids. Volatile silicone fluids are preferably oils chosen from cyclic or linear polydimethyl siloxanes containing from 3 to 9, preferably from 4 to 5 silicon atoms.

Cyclomethicone is the most preferred cyclic volatile silicone. Linear volatile silicone oils generally have viscosities less than about 5 centistokes at 25° C. while cyclic fluids typically have viscosities of less than about 10 centistokes.

Non-volatile silicone oils useful for the present invention include polyalkyl siloxanes, polyalkylaryl siloxanes and polyether siloxane copolymers. Non-volatile polyalkyl siloxanes useful herein include, for example, polydimethyl siloxanes with viscosities of from 5 to 100,000 centistokes at 25° C. Among the preferred non-volatile silicones are the polydimethyl siloxanes having viscosities from 10 to 400 centistokes at 25° C. These siloxanes are available, for example, from the General Electric Company as SF 1075 methyl phenyl fluid or from Dow Corning as 556 Cosmetic Grade Fluid.

The non-volatile polyalkylaryl siloxane fluids that may be used include, for example, polymethylphenylsiloxanes having viscosities of about 15 to 30,000 centistokes at 25° C.

Also includable are minor amounts of other ingredients commonly found in hair care compositions, such as anti-foam agents, antioxidants, proteins, preservatives, keratin amino acids, UV inhibitors, fragrances, coloring agents, buffering agents, polyols, and other moisturizing agents. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine.

(ii) hair fibre benefit agents. Examples are:
ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

The invention will now be further illustrated by the following, non-limiting Example:

EXAMPLE

An illustrative formulation according to the present invention is described below.

| INGREDIENT | WEIGHT % |
|---|---|
| Concentrate | |
| AMPHOMER ®[(1)] | 2.80 |
| Aminomethylpropanol | 0.46 |
| Perfume | 0.15 |
| Dextrose | 0.01 |
| Isoleucine | 0.01 |
| SILWET ® L-7602[(2)] | 0.08 |
| DC345[(3)] | 0.08 |
| Sodium benzoate | 0.20 |
| Water | 17.00 |
| Alcohol | balance |
| Propellant | |
| Hydrocarbon 2.7B | 15.00 |
| Dimethyl Ether | 30.000 |

[(1)]Octylacrylamide/acrylates/butylaminoethyl methacrylate copolymer, ex National Starch.
[(2)]Ethoxylated dimethicone copolyol ex OSi Specialities
[(3)]Cyclomethicone, ex Dow Corning

What is claimed is:
1. A single phase autophobic hairspray composition comprising:
a) 0.5% to 10% by weight of a film-forming hairspray resin;
b) 10 to 60% by weight of a mixed propellant system consisting of ($C_1$–$C_4$ alkyl ether) and a $C_3$–$C_5$ alkane selected from the group consisting of propane, isobutane, n-butane, and mixtures thereof;
c) 0.01% to 1.0% by weight of an autophobic hairspray additive selected from the group consisting of:
(i) alkyl-pendant silicone copolyols of formula (I):

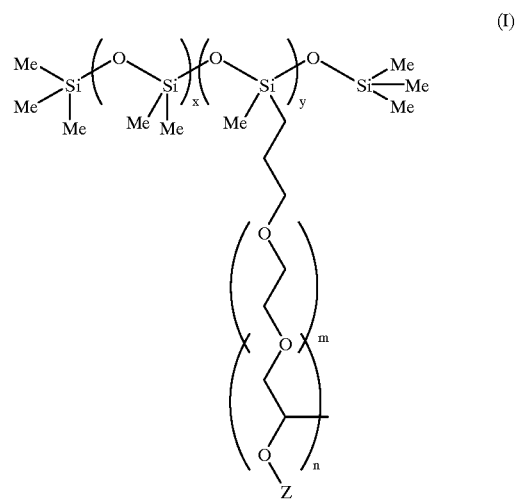

where m and n are integers of from 0 to 50, and x and y are integers chosen to give the copolyol a molecular weight of at least 600; Z is hydrogen or a C1–4 alkyl radical; Wherein Me stands for methyl;
(ii) dimethicone copolyols of formula (II):

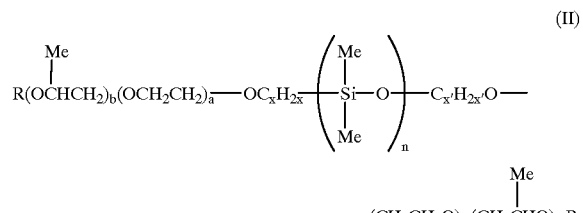

where n is an integer chosen to give the copolyol a molecular weight of at least 600;
x and x' are integers of from 1 to 12;
a, a', b, b' are integers of from 0 to 50, R is hydrogen or a C1-4 alkyl radical; and wherein me stands for methyl;

(iii) polydimethicone copolyols of formula (III):

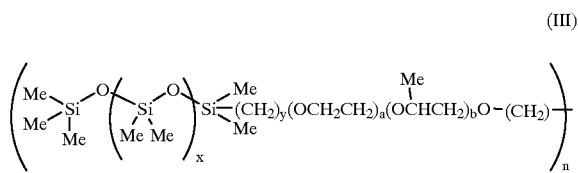

(III)

where x and n are integers chosen to give the copolyol a molecular weight of a least 500;
y is an integer of from 1 to 12, and
a and b are integers of from 0 to 50; and wherein me stands for methyl;
(iv) alkyl ethoxylates; and
(v) fluorosurfactants
which imparts autophobic behavior to the hairspray composition, and
d) 10% to 25% by weight water.

2. A hairspray composition according to claim 1, in which the film-forming hairspray resin is an amphoteric resin.

3. A hairspray composition according to claim 1, in which the weight ratio of hydrocarbon and di($C_1$–$C_4$ alkyl) ether is from 1:1 to 1:4.

4. A composition according to claim 2, wherein said amphoteric resin is octyl acrylamide/acrylates/butylaminoethyl methacrylate copolymer.

5. A composition according to claim 1, wherein said autophobic hairspray additive is an ethoxylated dimethicone copolyol.

6. A composition according to claim 3, wherein the weight ratio of hydrocarbon and di($C_1$-$C_4$ alkyl) ether is about 1:2.

7. A composition according to claim 1, wherein water content is 15 to 20% by weight of the total composition.

* * * * *